United States Patent [19]

Cooper

[11] 4,242,673
[45] Dec. 30, 1980

[54] OPTICAL PARTICLE DETECTOR

[75] Inventor: Glenn F. Cooper, Hingham, Mass.

[73] Assignee: American District Telegraph Company, Jersey City, N.J.

[21] Appl. No.: 885,369

[22] Filed: Mar. 13, 1978

[51] Int. Cl.³ .................................. G08B 17/10
[52] U.S. Cl. ........................ 340/630; 250/574; 356/439
[58] Field of Search ............... 340/628, 630; 356/439; 250/574

[56] References Cited

U.S. PATENT DOCUMENTS

| | | | |
|---|---|---|---|
| 1,877,279 | 9/1932 | Dawson | 340/630 X |
| 2,640,123 | 5/1953 | Cahusal et al. | 340/630 |
| 2,712,643 | 7/1955 | Hall | 250/209 X |
| 3,444,544 | 5/1969 | Pearson et al. | 340/630 X |
| 3,881,112 | 4/1975 | Roberts | 340/630 |
| 3,922,655 | 11/1975 | Lecuver | 340/630 |
| 4,021,792 | 5/1977 | Ludt et al. | 340/630 |

FOREIGN PATENT DOCUMENTS

| | | | |
|---|---|---|---|
| 625731 | 7/1949 | United Kingdom | 340/630 |
| 716654 | 10/1954 | United Kingdom | 340/630 |
| 919640 | 2/1963 | United Kingdom | 250/565 |

Primary Examiner—John W. Caldwell, Sr.
Assistant Examiner—Daniel Myer
Attorney, Agent, or Firm—James H. Grover

[57] ABSTRACT

A photoelectronic smoke detector has walls around a dark chamber to which smoke, but not light, is admitted, and through which light is directed from a source on a path to a limited area of a chamber wall. A first photocell views light scattered from the through path by particles in the path primarily and also receives background light scattered from the chamber wall outside the limited area. A second photocell is disposed to receive background light substantially only from the limited area and other areas outside the source light path. The first cell produces a first signal in response to background and particle-scattered light. The second cell produces a second signal corresponding to background scatter. The first and second cells, preferably photovoltaic photodiodes, are coupled in opposition in a circuit whose output consequently is substantially independent of the background light.

5 Claims, 5 Drawing Figures

OPTICAL PARTICLE DETECTOR

RELATED APPLICATION

Reference is made to application Ser. No. 885,370 of Glenn F. Cooper and Robert B. Enemark entitled LATCHING ALARM SMOKE DETECTOR, filed concurrently herewith and incorporated herein by reference.

BACKGROUND OF THE INVENTION

Known optical smoke and other particle detectors comprise a source whose light is directed on a path or beam which may be interrupted by smoke or other particles or media which scatter light from the directed path to a sensing photocell, the photocell responding to the scattered light by producing an electrical signal.

It is also well known to compensate for variations in the light source by employing a second photocell exposed to light direct from the source and connected in a circuit with the first photocell so that the response of the second cell to undesired light source variations cancels the effect of such variations on the first, smoke sensing, cell as disclosed for example in U.S. Pat. Nos. 2,301,367 and 3,409,885.

The object of the present invention, however, is to employ a second photocell in a way distinctly different from that described above in that the second cell is not exposed to light directly from the source, but rather the second cell is disposed so that it compensates not for light source variations, but instead compensates for the background light conditions in the dark chamber of a smoke detector, for example. These light background conditions are meant to include outside ambient light leaking into the chamber and such internal source light as is scattered from dark chamber walls outside the directed path from the source. The background light condition affects the total response of the smoke sensing photocell unduly when the background light sensed approaches the energy of the light scattered by smoke from the light beam or path. That is, the background light tends to mask the smoke scattered light and reduce the sensitivity of the detector to very low densities of smoke which occur early in a fire.

Thus the objects of the present invention are to increase the sensitivity of a particle detector to small changes in particle density, to permit reduction in the source light intensity, and to compensate for increase in background scattered light as dust and the like accumulate on the walls of the dark chamber.

STATEMENT OF INVENTION

According to the invention an optical particle detector comprises means, including a wall, forming a chamber; means for directing light on a path through the chamber; a first photocell disposed to respond primarily to light scattered from the path by particles in the path; a second photocell disposed to respond substantially to background light scattered from outside the through light path to produce a second electrical signal across the second cell; and circuit means coupling the two cells in opposition so as to produce an output signal substantially independent of background light scattered from outside the through light path.

Describing the disposition of the second cell to respond to scattered light from outside the source light through path distinguishes clearly from the previously known disposition of a second cell in a path optically direct from the source. The expression "through light path" describes the source light path through the air space of the chamber whence it can be scattered by particles, as compared to the limited wall area where the light path is incident on the dark chamber wall and whence background light is scattered.

DRAWING

DESCRIPTION

Figure 1:
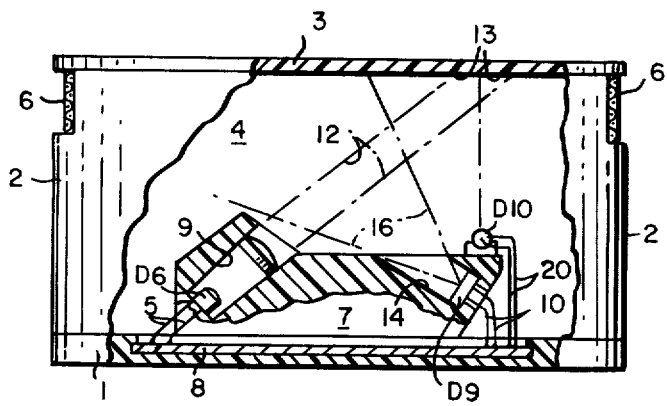
FIG. 1 is an elevation, partly broken away, of a smoke detector according to the invention.
Figure 3:
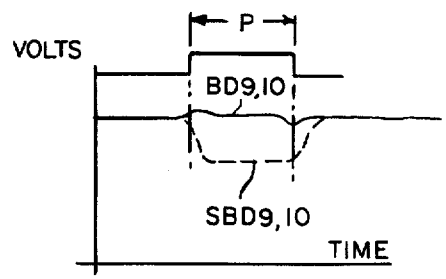

One form of optical smoke-detector according to the invention has an external housing shown diagrammatically in FIG. 1 as including a base 1, a circular sidewall 2 and a cover wall 3 enclosing a dark chamber 4 to which smoke has access through a porous foam sheet 6 (U.S. Pat. No. 3,947,303) or other labyrinthine structure which excludes light and insects. Adjacent the dark chamber is a chambered block 7 mounting the optical elements of the detector. Below the optical block is a circuit board 8 carrying the circuit components of the detector as shown in FIG. 3, except for the components in the optical block 7.

At one end of a light passage 9 in the optical block 7 is an infrared light emitting diode D6, for example RCA LED type SG 101A, with leads 5 to the circuit board 8. A lens 11 directs about 98% of the light from this source on a narrow path 12 through the air space within the chamber striking a limited area 13 of the housing wall 3 beyond the through path. The remaining 2% of source light is generally scattered throughout the dark chamber as is light incident on the limited area 13, the two constituting background light.

At the end of a second passage 14 oriented at 120° to the light passage 9 is a smoke sensing photodiode D9, Clairex Corporation type CLD56-1, a photovoltaic form of photocell with leads 10 to the circuit board. This photodiode D9 is primarily disposed to view the free path of light from the LED source D6 and respond to light scattered from smoke particles in the path within the view 16 of the photodiode D9. The smoke sensing diode D9 though shielded by the optical block 7 from light scattered directly from the limited area 13 beyond the through path 12 of the source light, LED D9, inevitably receives light scattered from that area 13 and from other areas of the side wall 2, the cover wall 3 and the optical block 7 including the second passage 14.

Although the undesired wall-scattered light is very low in intensity, so also is the smoke scattered light. Current national standards of smoke detector sensitivity require the detection of grey smoke which obscures 1.5% of the light through one foot. Such a smoke density will scatter somewhat less than 1.5% of the source light in all directions, and a considerably lower percentage will reach the smoke sensing cell D9.

Figure 2:
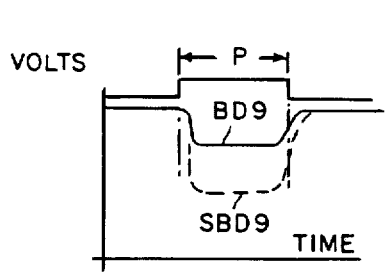
FIGS. 2 and 3 are time versus voltage graphs showing comparative signal voltages in the circuit of FIG. 3.

Shown somewhat idealized in FIG. 2 is a typical proportion between response to background light and smoke-plus-background light prior to the present inventions. As is explained with reference to FIG. 4, the LED source D6 is lighted for a pulse interval P. During this interval the relative voltage response of the smoke cell D9 in the absence of smoke is shown in FIG. 3 by the solid line curve BD9. In the presence of smoke-plus-background the relative voltage response is shown by the broken line curve SBD9. The proportion of background response BD9 to smoke-plus-background response SBD9 of the smoke sensing diode D9 varies with the intensity of light source and the configuration and optical characteristics of the dark chamber walls. But FIG. 2 fairly represents that, in the absence of compensation according to the present invention, the continuous response BD9 of the smoke cell 9 to background light is a substantial proportion of response SBD9 of the same cell to smoke scattered light and background light. That is the sensitivity of the cell is greatly reduced by its high response to background light. According to the present invention the loss of sensitivity illustrated by FIG. 2 can be largely overcome as shown in FIGS. 1, 3 and 4.

In FIG. 1 a second photovoltaic diode D10 is shown mounted on the top of the optical block 7 with leads 20 extending to the circuit board 8. The photodiode D10 is a plastic body diode, type 1N4001, a different, considerably less sensitive type than the smoke sensing diode D9 since it is exposed to the brightly illuminated limited area 13 beyond the through path 12 from the source light D6.

Figure 4:
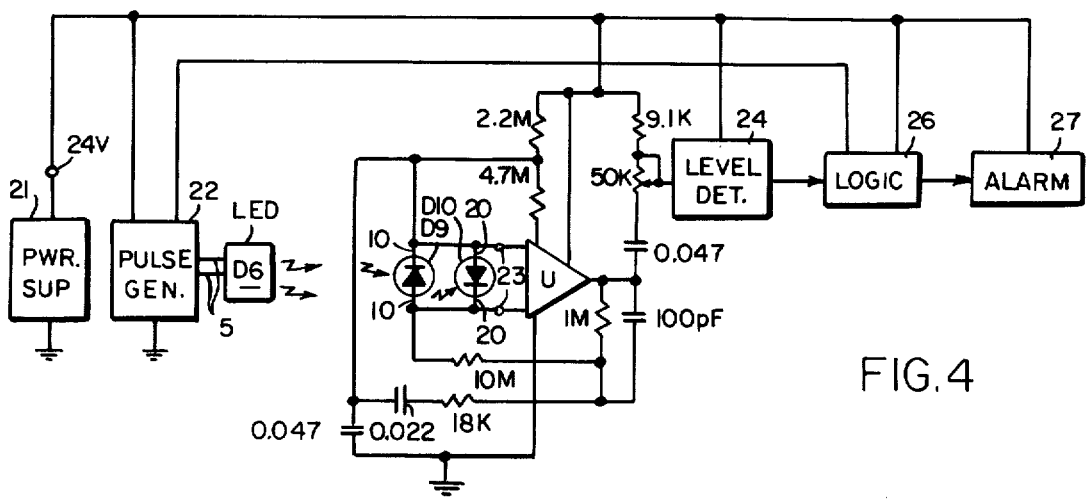
FIG. 4 is a schematic diagram of a circuit for the detectors of FIGS. 1 and 2.

As shown in FIG. 4, the first and second diodes are connected by their respective leads 10 and 20 so that they are in opposition at the input 23 to an operational amplifier U, type CA 30785 for example. That is, the anode of each photodiode is coupled either directly as shown, or indirectly to the cathode of the other diode. In FIG. 4 a 24 volt direct current power supply 21 energizes a pulse generator 22, which in turn flashes the LED light source D6 for about 150 microseconds pulse duration P at 2.5 second intervals, for example. The diodes D9 and D10 are thus pulsed with background light and also with scattered light if smoke is present. By virtue of the kinds of light to which they are exposed and of their coupling in opposition their voltages at the amplifier input 23 take the form shown idealized in FIG. 3. In the no-smoke condition the solid line voltage BD9, 10 resultant from the coupled responses of the photocells D9 and D10 to the background light during the light pulse P is now substantially level at the applied voltage from the power supply 21, with insignificant deviations at the beginning and end of the pulse P duration. In the presence of smoke the broken line voltage SBD9, 10 resultant from the coupled responses of both photocells D9, 10 to smoke scattered and background light is much like the single cell response SBD9 of FIG. 2. But the ratio between the no-smoke and smoke response is much greater because the solid line no-smoke reponse BD9, D10 is inconsiderable relative to the broken line smoke response SBD9, 10. Consequently very low densities of smoke, e.g. under 1% obscuration per foot, can be detected sensitively and accurately at lowered light output, hence lower power consumption by the LED source D6.

The coupled, difference voltage smoke signal is amplified by the operational amplifier U whose associated resistive and circuit components have values indicated in a conventional way. The amplified output of the operational amplifier is applied through a 50 kilohm potentiometer to a level detector 24 whose threshold is set by the potentiometer to correspond to a predetermined smoke density. When the level detector's threshold is exceeded by the amplifier output the level detector applies a pulse of data to a logic circuit 26 simultaneously with a clock pulse from the pulse generator 22. The logic circuit then triggers a smoke alarm 27 which may be a local visible or audible alarm or a relay to a remote alarm device.

Figure 5:
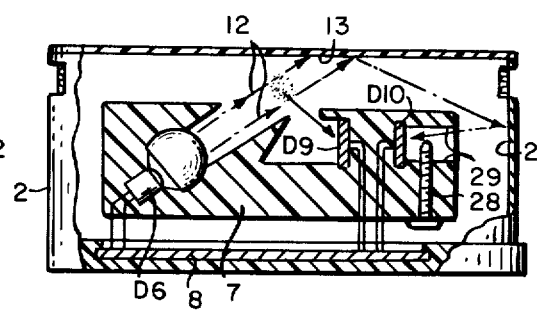
FIG. 5 is a similar elevation of a second form of the invention.

FIG. 5 shows a smoke detector with components and voltages like those of FIG. 1, but differing in that a second photodiode D10* is of the same order of sensitivity as the first photodiode D9, the second diode is shielded from light scattered from the through path 12 and the shield is in the form of an adjustable screw 28 varying light reaching the second diode through a passage 29 in the optical block 8. The second photodiode of FIG. 5 also receives light more indirectly scattered from the housing wall 3 and the sidewall 2 than in the case of FIG. 1.

The detectors of FIG. 5 and FIG. 1 both provide the advantage of significantly greater sensitivity to the very slight changes from zero to less than 1% smoke obscuration per foot. Greater background light can be tolerated than hitherto, and the size of the dark chamber and hence the outside dimension of the detector can be reduced without sacrifice of reliability. The LED light source power requirement can be reduced while the sensitivity of the smoke sensing cell D9 to variation in LED current and efficiency is minimized. During the life of the detector extended over many years, increase in background light scattering due to accumulation of dust on the dark chamber walls is compensated by the location of the second cell so as to view light primarily from outside the through path of source light, and the coupling of the first and second cells in opposition in the amplifying circuit.

It should be understood that the present disclosure is for the purpose of illustration only and that this invention includes all modifications and equivalents which fall within the scope of the appended claims.

I claim:
1. An optical particle detector comprising:
   means including wall means forming a chamber;
   means for directing light on a path through the chamber;
   a first photovoltaic cell optically disposed to respond primarily to background light scattered from the wall means and from the path by particles in the path to produce a first signal proportional to particle scattered light and background light;
   a second photovoltaic cell disposed outside the through path and optically disposed to view substantially entirely background light to which the first cell is exposed and which is scattered from the wall means around and outside the through light path to produce a second electrical signal across the second cell proportional to background light; and
   circuit means connecting the two cells with the anode of each cell coupled to the cathode of the other cell so as to produce an output signal substantially only proportional to particle scattered light and substantially independent of background light scattered from outside the through light path.

2. A detector according to claim 1 wherein the light means and first cell are mounted in an enclosing optical block, and the second cell is outside the block.

3. A detector according to claim 1 including means adjustably shielding the second cell from scattered light.

4. A detector according to claim 1 wherein the circuit means includes amplifier means responsive to an output signal above a predetermined threshold to produce an electrical alarm signal.

5. A detector according to claim 4 including a common power supply for the light source and amplifier means.

* * * * *